United States Patent [19]
Margolis

[11] Patent Number: 5,288,465
[45] Date of Patent: Feb. 22, 1994

[54] CASSETES FOR ELECTROPHORETIC GELS

[75] Inventor: Joel Margolis, Greenwich, Australia

[73] Assignee: Gradipore Limited, Pyrmont, Australia

[21] Appl. No.: 949,293

[22] Filed: Sep. 22, 1992

[51] Int. Cl.⁵ .............................. B01L 3/00
[52] U.S. Cl. .................. 422/102; 422/681; 422/99; 422/101; 204/299 R
[58] Field of Search .............. 422/102, 101, 68.1, 422/99; 204/299 R, 182.8; 220/507, 555; 206/569, 509, 528

[56] References Cited

U.S. PATENT DOCUMENTS

| | | | |
|---|---|---|---|
| 3,450,624 | 6/1969 | Natelson | 204/182.8 |
| 3,875,045 | 4/1975 | Bergrahm et al. | 204/182.8 |
| 3,879,280 | 4/1975 | Peterson et al. | 204/299 R |
| 4,035,377 | 7/1977 | Detroy | 204/299 R |
| 4,337,131 | 6/1982 | Vesterberg | 204/182.8 |
| 4,548,869 | 10/1985 | Ogawa et al. | 935/16 |
| 4,828,801 | 5/1989 | Lombardy wife Alric et al. | 422/102 |
| 4,909,918 | 3/1990 | Bambeck et al. | 204/182.8 |
| 4,919,784 | 4/1990 | Yetman | 204/182.8 |

Primary Examiner—James C. Housel
Assistant Examiner—Jan M. Ludlow
Attorney, Agent, or Firm—Allegretti & Witcoff, Ltd.

[57] ABSTRACT

A cassette for holding an electrophoretic gel. The cassette has two substantially planar wall members formed of a synthetic plastics material, each wall member having two sides and two ends. The wall members are formed integrally along each side with an array of interdigitating ribs and grooves which releasably hold the wall members in substantially parallel array spaced apart sufficiently to define between them an electrophoretic gel receiving space. The ribs and grooves also serve to form a substantially fluid tight seal down each side of the gel receiving space. A plurality of ribs extend between the upper edges of the two wall members to define a series of wells above the gel into which samples to be electrophoretically separated may be placed.

7 Claims, 2 Drawing Sheets

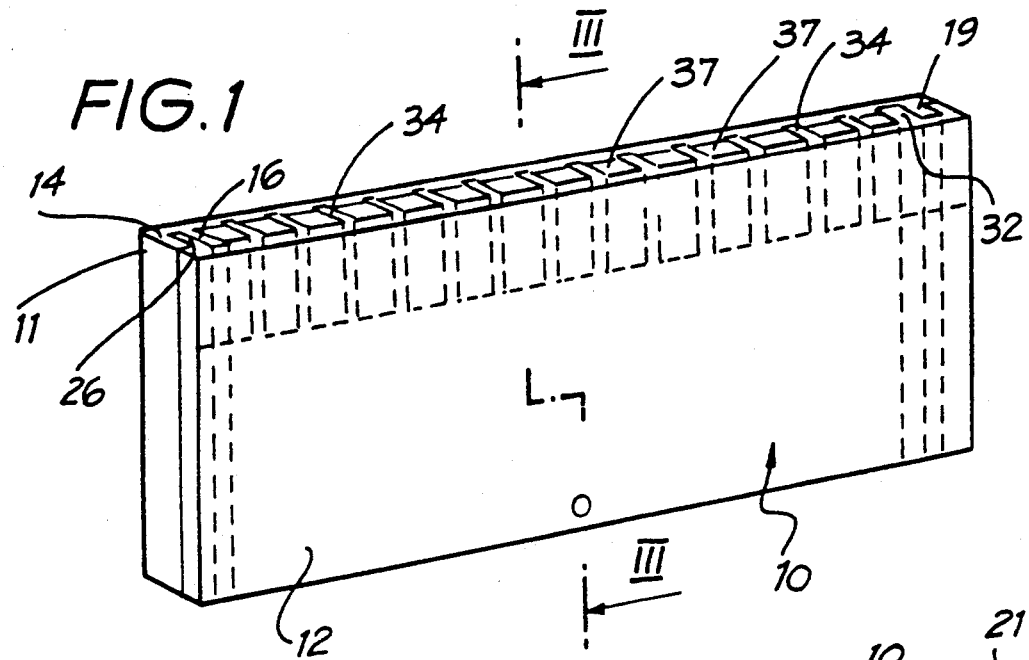
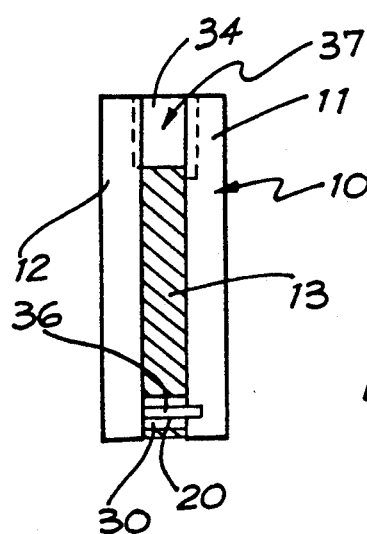

CASSETES FOR ELECTROPHORETIC GELS

BACKGROUND OF THE INVENTION

1. Field of the Invention

The present invention relates to cassettes for holding electrophoretic gels and, more particularly, to cassettes for electrophoretic gels formed of two parts which incorporate means to hold the two parts of the cassette together.

2. Background Art

Electrophoretic gels are gels, usually of polyacrylamide, which are used for the separation of proteins and other macromolecular compounds. The material to be separated is placed at one end of the gel and a direct electrical field is applied between the ends of the gel causing the molecules to migrate through the gel at rates dependant upon the molecular size of the compound.

Electrophoretic gels have been traditionally sold sandwiched between a pair of sheets of glass. The sheets of glass are held in an appropriate parallel spaced relationship by a pair of spacers positioned down each side of the gel. A mixture of compounds to be separated is normally introduced into one of a number of small wells formed in an upper edge of the gel before the direct current field is applied to the gel. It is usual to run a number of such mixtures simultaneously on an electrophoretic gel in a side by side arrangement. For this purpose one mixture is placed in each of a series of wells formed in the upper edge of the gel. The wells in the upper edge of the gel are usually formed by pushing a comb into the upper edge of the gel to form the wells at the time the gel is to be used or a series of small tubes are pushed into the upper edge of the gel and themselves form the wells.

The use of glass in forming the cassette has had the advantage of rigidity, good gel adhesion, chemical compatibility with the gel and good heat conductivity. It has had the disadvantage of high production cost for a disposable item and the relatively ungainly methods for forming the wells as has been described above. It has been suggested previously to form a cassette from a synthetic plastics material, however, these proposals have not been successful for a number of reasons. It proved difficult to form the walls of the cassette with sufficient rigidity while still being sufficiently thin for good heat transfer and ease of manufacture. There has also been a problem in ensuring sufficient adhesion of the gel to the plastics material. In the absence of good adhesion the gel is liable to slip out of the cassette during electrophoresis. Some plastics materials have also been found to inhibit polymerization of the gel monomer solutions flowed into the cassette during formation of the gel.

SUMMARY OF THE INVENTION

The present invention consists of a cassette for holding an electrophoretic gel, comprising first and second substantially planar wall members each having two sides and two ends, connecting means formed integrally with and along the sides of one or each of the wall members, the connecting means being adapted to hold the wall members in substantially parallel planes spaced apart sufficiently to define between them an electrophoretic gel receiving space, and serving to form a substantially fluid tight seal between the sides of the wall members when they are held together, and a plurality of dividing ribs on one or each of the wall members extending from one end of the member or members substantially parallel to at least one of the side edges thereof and adapted to extend into the space when the wall members are held together so as to subdivide at least one end of the space into a plurality of substantially parallel wells.

In a preferred embodiment of the invention the cassette is formed from a synthetic plastics material selected from the group comprising polyvinylchloride and polyethylene terephthalate G. It has been found that these materials do not inhibit gel polymerization while offering the desired properties of rigidity and heat transfer. Any problems of gel adhesion to the plastics material can be overcome by the provision of physical gel entrapment as will be described later in this specification.

The wall members are preferably rectangular in shape with the ends longer than the sides. The connecting means down either side of each wall member preferably comprises a rib and a groove adapted to sealingly interdigitate with the corresponding groove and rib respectively on the complementary other wall member of the cassette. If desired, additional connection means in the form of pins formed integrally in one wall member and adapted to engage in complementary holes in the other wall member of the cassette may be utilized.

It is desirable that the cassette is provided, intermediate its side edges and adjacent its lower end, with a pin on one wall member and a corresponding recess to receive the pin in the other. The pin and recess are so dimensioned as to maintain the correct spacing between the wall members. This pin and recess also serve to maintain the gel in position in the cassette during the electrophoresis process.

The cassette must be able to be broken open to allow access to the gel for the purpose of staining it to reveal the location in the gel of the separated proteins and other macro-molecules. The connecting means therefore preferably only releasably connects together the side edges of the wall members. The wall members may then be manually separated from one another after the electrophoretic separation has occurred to provide access to the gel.

The dividing ribs preferably extend from one of the wall members of a cassette into shallow grooves in the other wall member of that cassette. It is possible, however, to use ribs on each of the wall members which abut or otherwise cooperate to divide one end of the cassette into a plurality of parallel channels. Each of the channels formed by the ribs cooperates with the gel which is introduced into the cassette no more than part way up the channels to form a plurality of side by side wells into which materials to be separated may be introduced. The provision of these preformed wells simplifies the use of the gel and makes the electrophoretic separation method more efficient.

BRIEF DESCRIPTION OF THE DRAWINGS

A preformed embodiment of the invention is hereinafter described with reference to the accompanying drawings in which:

FIG. 1 is a perspective view of an assembled cassette for an electrophoretic gel according to the present invention;

FIG. 2 is a plan view of the cassette of FIG. 1;

FIG. 3 is a sectional view through the cassette of FIG. 1 along section III—III;

DETAILED DESCRIPTION

Figure 4:
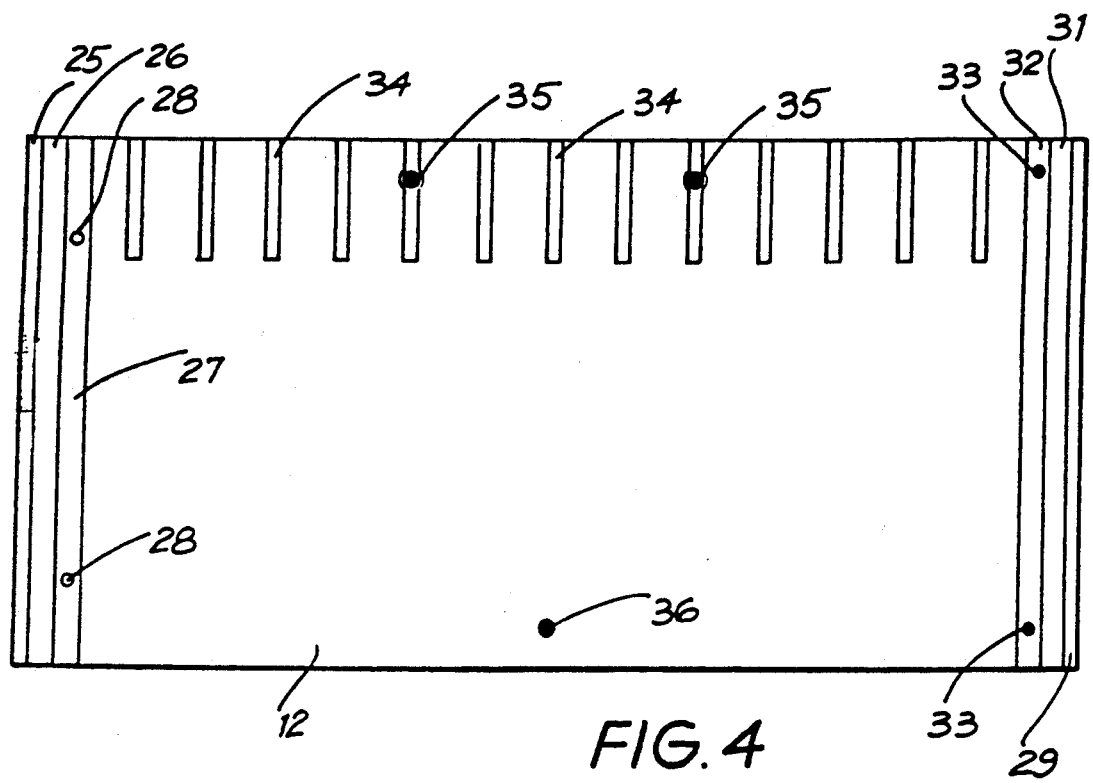
FIG. 4 is an elevational view of the inside face of one of the walls of the cassette of FIG. 1.

The cassette 10 shown in the drawings comprises two wall members 11 and 12 releasably joined together and enclosing an electrophoretic gel 13. The wall members 11 and 12 are made of polyethylene terephthalate G. The electrophoretic gel 13 may be of any suitable type but is preferably a polyacrylamide gel having a gradient density which increases from the top to the bottom of the gel.

Figure 5:
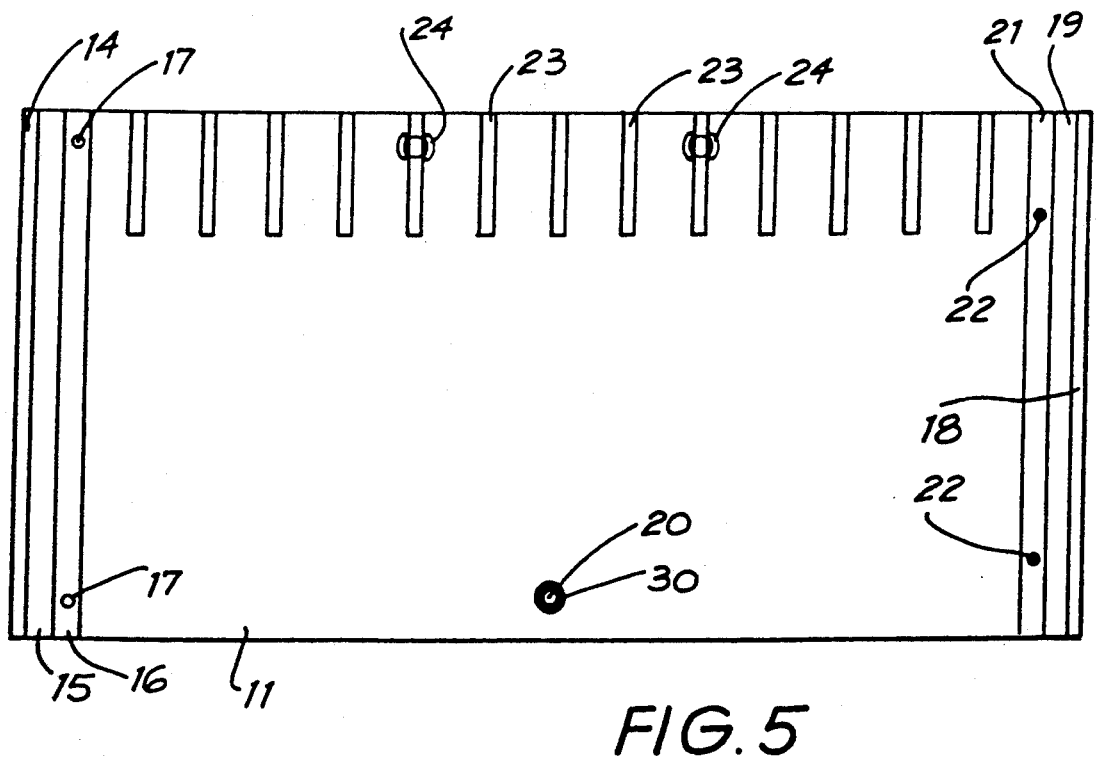
FIG. 5 is an elevational view of the inside face of the other of the walls of the cassette of FIG. 1.

As is best seen in FIG. 5, the wall member 11 is rectangular in shape with a length greater than its depth. On its left hand side edge (as seen in FIG. 5), the wall member 11 is formed with a shallow rib 14, which stands proud of the inside face of the wall member 11 by the thickness of the gel 13. Immediately adjacent and parallel to this is a recess 15 and then a deeper rib 16. The rib 16 is formed with two spaced apart bores 17. The right hand side edge (as seen in FIG. 5) of the wall member 11 is formed with a narrow ledge 18, inside this and parallel to it is a rib 19 and then a recess 21. The recess 21 is formed with a pair of spaced apart pins 22. Along the upper edge of the wall member 11 is a series of shallow grooves 23. The grooves 23 are equally spaced apart and lie parallel to the side edges of the wall member 11. Two spaced apart ones of the grooves 23 are bounded by hemi-cylindrical bosses 24. Intermediate its sides and adjacent its lower edge, the wall member 11 is formed with a base 20 surrounded by a cylindrical lip 30 having a height equal to the thickness of the gel 13.

The wall member 12 is essentially similar in shape to the wall member 11 but is complementary to it. The left hand side edge of the wall member 12 (as seen in FIG. 4) is formed with a shallow rib 25 which stands proud of the inside face of the wall member 12 by the thickness of the gel 13 and is of a width equal to the ledge 18 of wall member 11. Inside and adjacent the rib 25 is a parallel recess 26 and inside that a rib 27. The rib 27 is formed with a pair of bores 28 adapted to receive the pins 22 of the recess 21 of wall member 11. The right hand side edge of the wall member 12 (as seen in FIG. 4) is formed with a ledge 29 of the same width as rib 14 on the wall member 11. Inside the ledge 29 is a rib 31 and inside that a recess 32 carrying a pair of spaced apart pins 33 adapted to engage in bores 17 in the rib 16 of the wall member 11.

The wall member 12 is formed along its upper edge with a plurality of thin ribs 34. These ribs 34 are so spaced and dimensioned that their free ends rest in respective ones of the grooves 23 of the wall member 11. The ribs 34 which engage with the grooves 23 which are bounded by the hemi-cylindrical bosses 24 are formed with corresponding hemi-cylindrical protuberances 35 which engage in a friction fit with the respective ones of the hemi-cylindrical bosses 24. The wall member 12 is formed intermediate its sides and adjacent its lower edge with an inwardly directed pin 36 adapted to form a friction fit with bore 20 in the wall member 11.

In use the wall members 11 and 12 are clipped together with the ribs 16 and 19 of the wall member 11 engaging in a friction fit in grooves 26 and 32 in wall member 12 and similarly the ribs 27 and 31 of wall member 12 engage in a friction fit in grooves 15 and 21 of wall member 12. These interdigitating ribs and grooves form a substantially fluid tight seal down each side of the cassette 10. They also serve, together with ribs 34, and pin 36, to maintain the inside surfaces of the wall members 11 and 12 in spaced apart substantially parallel planes defining therebetween a gel receiving space. The gel 13 is filled into this space from the bottom of the cassette up to or slightly above the lower edge of ribs 34.

The wall members 11 and 12, the ribs 34 and the top surface of the gel 13 together serve to define a plurality of side by side wells 37 adapted to receive samples to be separated electrophoretically.

When the cassette has been used it may be split apart by pulling on the two wall members 11 and 12 to expose the gel therebetween for staining.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A cassette for holding an electrophoretic gel, comprising:

first and second substantially planar wall members each having two sides and first and second ends, connecting means formed integrally with and along the sides of each of the wall members, the connecting means being adapted to hold the first and second wall members in substantially parallel planes spaced apart sufficiently to define between them an electrophoretic gel receiving space that has an opening between the first ends of the first and second wall members and an opening between the second ends of the first and second wall members, and a plurality of dividing ribs on one or each of the wall members extending from the first end of the member or members substantially parallel to at least one of the sides thereof and adapted to extend into the space so as to subdivide at least one end of the space into a plurality of substantially parallel wells, wherein the connecting means serve to releasably hold the wall members together and wherein the connecting means comprise sealing means for forming a substantially fluid tight seal between the sides of the wall members, the sealing means consisting essentially of a sealing rib and sealing groove along each side of each of the wall members, the respective sealing ribs and sealing grooves of the wall members being adapted to frictionally interdigitate.

2. A cassette as claimed in claim 1 in which the connecting means additionally includes at least one pin formed integrally with at least one of the wall members and disposed in at least one of said sealing grooves therein, the pin being adapted to frictionally engage in a bore formed in one of said sealing ribs of the other of said first and second wall members.

3. A cassette as claimed in claim 1 in which the connecting means additionally includes a pin on one of the wall members intermediate the sides thereof and adjacent the second end thereof and a recess in the other wall member intermediate the sides thereof and adjacent the second end thereof adapted to frictionally engage the pin.

4. A cassette as claimed in claim 1 in which the cassette is made from a synthetic plastic material selected from the group comprising polyvinylchloride and polyethylene terephthalate G.

5. A cassette as claimed in claim 1 in which the dividing ribs are formed integrally with one of the wall members and free ends of the dividing ribs engage with respective shallow dividing grooves in the other wall member.

6. A cassette as claimed in claim 5 in which at least one of the dividing ribs is adapted to frictionally engage at a free end of that dividing rib with complementary engagement means on the other wall member.

7. A cassette as claimed in claims 1, 2, 3, 5, 6 or 4 in which the gel receiving space contains an electrophoretic gel, the gel extending above the lower edge of the dividing ribs.

* * * * *